US011571442B2

(12) United States Patent
Molins Albanell et al.

(10) Patent No.: US 11,571,442 B2
(45) Date of Patent: Feb. 7, 2023

(54) TEAT SEAL FORMULATION

(71) Applicant: Zoetis Broomhill IP Limited, County Dublin (IE)

(72) Inventors: Francisco Javier Molins Albanell, Blackrock (IE); Brendan Gerard Smith, Clontarf (IE); James Kennedy, Athlone (IE); Fiona Ní Chearúil, Greystones (IE)

(73) Assignee: Zoetis Broomhill IP Limited, Loughlinstown (IE)

( * ) Notice: Subject to any disclaimer, the term of this patent is extended or adjusted under 35 U.S.C. 154(b) by 248 days.

(21) Appl. No.: 15/771,884

(22) PCT Filed: Oct. 19, 2016

(86) PCT No.: PCT/EP2016/075044
§ 371 (c)(1),
(2) Date: Apr. 27, 2018

(87) PCT Pub. No.: WO2017/071998
PCT Pub. Date: May 4, 2017

(65) Prior Publication Data
US 2018/0303868 A1   Oct. 25, 2018

(30) Foreign Application Priority Data
Oct. 29, 2015   (EP) .................................. 15192207

(51) Int. Cl.
*A61K 9/00* (2006.01)
*A61K 31/765* (2006.01)
*A61K 47/02* (2006.01)
*A61K 47/32* (2006.01)
*A61K 33/14* (2006.01)
*A61K 33/06* (2006.01)
*A61K 47/12* (2006.01)

(52) U.S. Cl.
CPC .......... *A61K 31/765* (2013.01); *A61K 9/0041* (2013.01); *A61K 33/06* (2013.01); *A61K 33/14* (2013.01); *A61K 47/02* (2013.01); *A61K 47/12* (2013.01); *A61K 47/32* (2013.01)

(58) Field of Classification Search
CPC .. A61K 9/0014; A61K 9/0017; A61K 9/0021; A61K 31/765
See application file for complete search history.

(56) References Cited

U.S. PATENT DOCUMENTS

| 4,393,080 A | * | 7/1983 | Pawelchak | C09J 7/38 428/355 R |
|---|---|---|---|---|
| 5,093,387 A | | 3/1992 | Schobel et al. | |
| 5,750,591 A | * | 5/1998 | Clarke | A61K 6/35 523/120 |
| 6,166,102 A | * | 12/2000 | Ahn | C09J 135/08 523/120 |
| 2005/0191270 A1 | * | 9/2005 | Gruening | A61K 9/0019 424/78.3 |
| 2006/0025494 A1 | * | 2/2006 | Gasman | A61K 6/35 523/120 |
| 2014/0222067 A1 | * | 8/2014 | Ericson | A61B 17/0057 606/213 |

FOREIGN PATENT DOCUMENTS

| EP | 1 803 788 A1 | 7/2007 | |
|---|---|---|---|
| WO | WO 92/09289 A1 | 5/1992 | |
| WO | WO 01/81437 A1 | 11/2001 | |
| WO | WO 2005/086641 A2 | 9/2005 | |
| WO | WO 2005/086641 A3 | 9/2005 | |
| WO | WO 2008/045920 A2 | 4/2008 | |
| WO | WO 2008/045920 A3 | 4/2008 | |
| WO | WO 2010/065747 A2 | 6/2010 | |
| WO | WO 2010/065747 A3 | 6/2010 | |
| WO | WO-2010065747 A2 * | 6/2010 | ............. A01N 59/16 |

OTHER PUBLICATIONS

Benson (Use of radiation in biomaterials sciences, Nuclear Instruments and Method sin Physics Research B 191 (2002) 752-757) (Year: 2002).*
International Search Report and Written Opinion dated Dec. 19, 2016, in International Patent Application No. PCT/EP2016/075044 (15 pages).

* cited by examiner

*Primary Examiner* — Micah Paul Young
(74) *Attorney, Agent, or Firm* — Finnegan, Henderson, Farabow, Garrett & Dunner, LLP

(57) ABSTRACT

A seal formulation for forming a physical barrier in the teat canal of a non-human animal for prophylactically controlling infection of a mammary gland by a mastitis-causing organism comprises a polymer in a gel base wherein the polymer is a lower alkyl vinyl ether-maleic anhydride copolymer or a salt derivative thereof. The lower alkyl vinyl ether-maleic anhydride copolymer salt derivative may comprise at least one cationic ion including monovalent, bivalent or trivalent cations and mixtures thereof.

18 Claims, 2 Drawing Sheets

TEAT SEAL FORMULATION

The present application is a national stage application under 35 U.S.C, § 371 of International Application No. PCT/EP2016/075044, filed Oct. 19, 2016, which claims priority of European Patent Application No. 15192207.7, filed Oct. 29, 2015, the contents of which is incorporated herein by reference in its entirety.

INTRODUCTION

This invention relates to a seal formulation for forming a physical barrier in the teat canal.

An intra-mammary teat sealant containing bismuth subnitrate in a gel base is known. The teat sealant may be used in conjunction with an antibiotic for prophylaxis or treatment of mastitis (GB 2273441A). It is also known to use the teat sealant on its own as a prophylactic treatment to protect against ingress of pathogens during an animal's dry period (WO9826759A).

These known teat seals have been proven to be highly effective over many years. One potential issue however is that if, on completion of the protective period, all of the seal is not fully stripped out of the teat, small amounts of residual teat sealant containing bismuth subnitrate can present during subsequent milkings and can adhere to the milking machine lines.

It is a challenge to provide a teat sealant which can be readily formulated, delivered into the teat canal, which will form an effective seal whilst being reliably stripped out of the teat canal when no longer required.

STATEMENTS OF INVENTION

According to the invention there is provided use of a seal formulation, comprising a polymer in a gel base, in the preparation of a medicament for forming a physical barrier in a teat canal for prophylactically controlling infection of a mammary gland in a non-human animal by a mastitis-causing organism, wherein the polymer is a lower alkyl vinyl ether-maleic anhydride copolymer or a salt derivative thereof.

According to the invention there is also provided a seal formulation for forming a physical barrier in the teat canal of a non-human animal comprising a polymer in a gel base wherein the polymer is a lower alkyl vinyl ether-maleic anhydride copolymer or a salt derivative thereof. The seal is used to treat, prevent or supress infection with a mastitis causing organism.

In one embodiment the lower alkyl vinyl ether-maleic anhydride copolymer salt derivative comprises at least one cationic ion including monovalent, bivalent or trivalent cations and mixtures thereof. The cationic ion may be calcium, sodium or mixtures thereof.

In one case the polymer is a methyl vinyl ether-maleic anhydride copolymer or a salt derivative thereof.

The copolymer may be a mixed calcium and sodium salt derivative of a methyl vinyl ether-maleic anhydride copolymer.

In one embodiment the seal formulation contains from 10% to 60% by weight of the polymer. The seal formulation may contain from 20% to 60% by weight of the polymer. The seal formulation may contain from 30% to 55% by weight of the polymer.

In one embodiment the seal formulation further comprises a viscosity enhancing agent. The viscosity enhancing agent may comprise zinc oxide. In one case the seal formulation contains from 1% to 35% of the viscosity enhancing agent. The seal formulation may contain from 5% to 25% of the viscosity enhancing agent. The seal formulation may contain from 5% to 20% of the viscosity enhancing agent.

In one embodiment the seal formulation further comprises a thixotrophic agent. The seal formulation may contain from 0.1% to 1% of the thixotrophic agent. The seal formulation may contain from 0.4 to 0.8% of the thixotrophic agent. In one case the thixotrophic agent comprises fumed silica.

In one embodiment the base is a gel based on aluminium stearate.

In one case the base includes liquid paraffin as a vehicle. The seal formulation may contain from 30% to 50% of the base.

The lower alkyl vinyl ether-maleic anhydride copolymer and derivative thereof useful in the invention dissolve slowly and contribute adhesive properties as they take up water. Such lower alkyl vinyl ether-maleic acid polymers may be obtained by polymerizing a lower alkyl vinyl ether monomer with maleic anhydride to yield the corresponding lower alkyl vinyl ether-maleic anhydride polymer which is readily hydrolyzable to the acid polymer. The term "lower alkyl" includes C1-C8 alkyl, C1-C6 alkyl, and C1-C4 alkyl. Salt forms of the copolymers can be used. For example, salt forms of the copolymers may be used in which the cationic ion is a monovalent, bivalent, or trivalent cation. Combinations of such salts may also be used. In particular, sodium and calcium forms of the copolymer salts and mixtures of such salt forms may be used.

A lower alkyl vinyl ether-maleic anhydride copolymer and derivative thereof with a weight average molecular weight of about 200,000 to 2,000,000 is preferably used.

One example of such a polymer is GANTREZ MS-955 salt which is available from International Specialty Products. This copolymer has both sodium and calcium salts in one molecule and is supplied as a powder. The copolymer is slowly soluble in water resulting in amber-coloured solutions with high viscosity and adhesion. The divalent calcium ion lightly crosslinks the material through ion bridges to reduce its solubility and increase its cohesive strength and viscoelasticity. It is believed that the repeating units may be represented as:

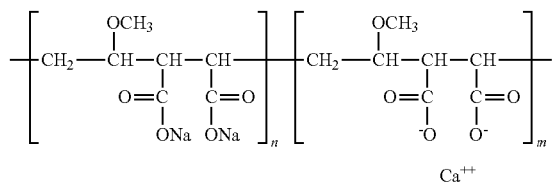

The approximate weight average molecular weight of GANTREZ MS-955 is 1,000,000 and its Brookfield viscosity (mPaS (11.1% solids aq.)) is 700-3000.

The formulation includes a thixotrophic agent or rheology modifier or emulsifier. One such is fumed silica which is also known as anhydrous colloidal silica. It is available from Evonik under the Trade Name Aerosil. It is also available from Cabot Corporation (Cab-o-sil) and Wacker Chemie—Owens Corning and OCI (Konasil).

The formulation also includes Zinc Oxide.

Zinc oxide has been used effectively in the treatment of many skin disorders. Zinc oxide has a mild astringent and antiseptic action. Zinc oxide is a Category I skin protector, and promotes healthy skin. Zinc oxide is used for treatment of skin diseases and infections such as eczema, impetigo, ringworm, varicose ulcers, pruritus and psoriasis. It is believed that Zinc oxide regulates the activity of oil glands and is required for protein, DNA and RNA synthesis and collagen and other irritants The invention provides a bio-adhesive teat seal which provides an effective physical barrier to the teat canal of cattle for the prevention of intramammary infections throughout the dry period.

An effective teat seal of the invention has the following properties

Non toxic, biocompatible, and capable of being sterilised.

Persistent—the seal should remain in situ for the duration of the dry cow period Consistency—the seal should not break up within the teat Ease of removal—at the end of the dry period the seal should be easily removable from the udder and not give rise to persistent residues of the seal If an antibiotic is used in association with the seal, the seal should be compatible with the antibiotic formulation.

Radiopaque

Ease of delivery

DETAILED DESCRIPTION

Figure 1:
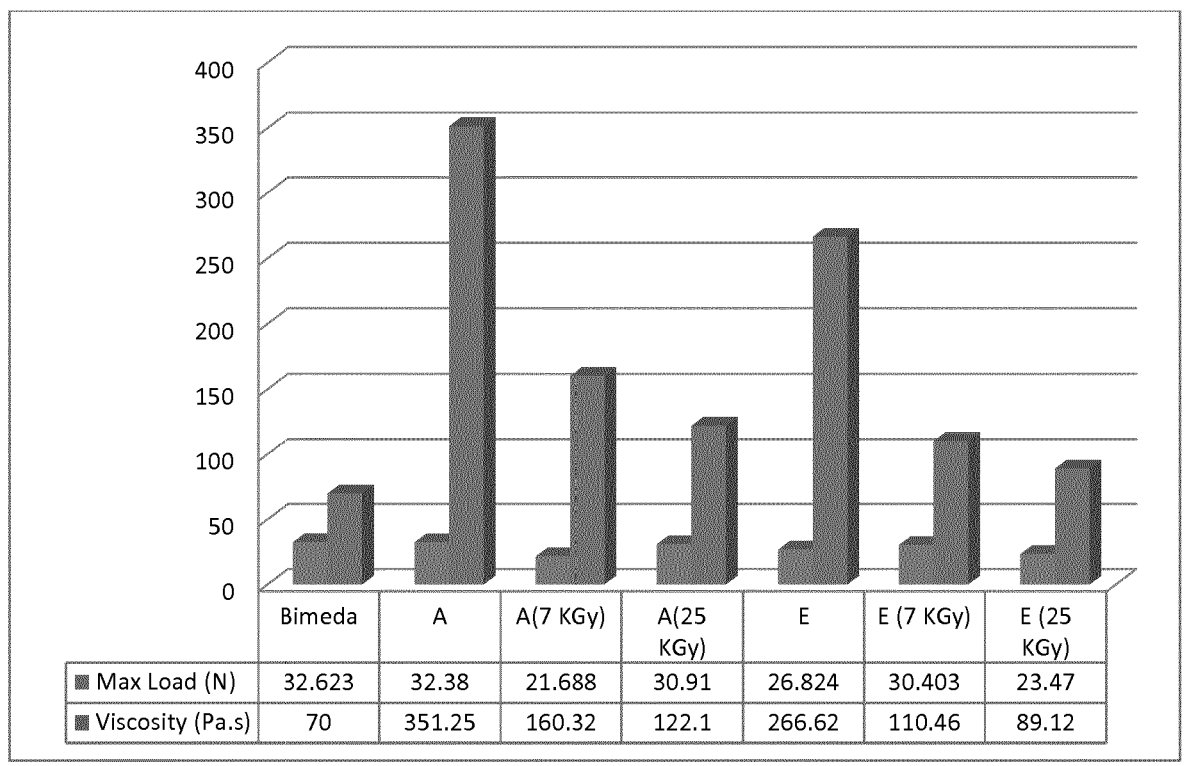
FIG. 1 is a bar chart showing comparative analysis between the max injection force and the viscosities of formulations (A) and (E) as well as the control sample.

The invention will be more clearly understood from the following description thereof given by way of example only.

Gantrez AN-169

Gantrez AN-169, is a water-insoluble white powder. The polymeric anhydride hydrolyses to produce a transparent solution of the free acid. Four standard (AN) grades are available, each differentiated by molecular weight ranging from 200,000 to 2 million.

Various Grades of the Gantrez AN Product Range

| Typical Properties | AN-119 | AN-903 | AN-139 | AN-169 |
|---|---|---|---|---|
| Appearance | White, free-flowing powder | White, free-flowing powder | White, free-flowing powder | White, free-flowing powder |
| Approx. Mw | 200,000 | 800,000 | 1,000,000 | 2,000,000 |
| Brookfield Viscosity, mPa · S | 15 | 30 | 40 | 85 |
| 5%/10% solids (Hydrolized) | 35 | 100 | 145 | 1400 |

The grade used had a molecular weight of 2,000,000 and the chemical structure is

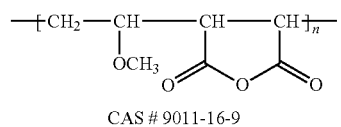

CAS # 9011-16-9

Chemical Structure of Gantrez AN-169

Experiment 1

4 g of the polymer was added to 10 ml of water and stirred
Outcome: Did not dissolve
4 g of the polymer was added to 10 ml of Milk and stirred
Outcome: Did not dissolve
Conclusion: The hydrophobic nature of polymer used in a suitable vehicle could be a potential seal.

Experiment 2

1 g of the polymer was added to 1 ml of water and stirred
Outcome: Did not dissolve—formed a paste
1 g of the polymer was added to 2 ml of water and stirred
Outcome: Formed a viscous paste, felt lubricious
Conclusion: The hydrophobic nature of polymer used in a suitable vehicle could be a potential seal.

Gantrez MS-955

An alternative polymer, MS-955, was also investigated as a potential novel teat sealant system. Gantrez MS-955 polymer is a mixed sodium and calcium salt of methyl vinyl ether and maleic anhydride copolymer that may be synthesised from Gantrez AN169 as follows:

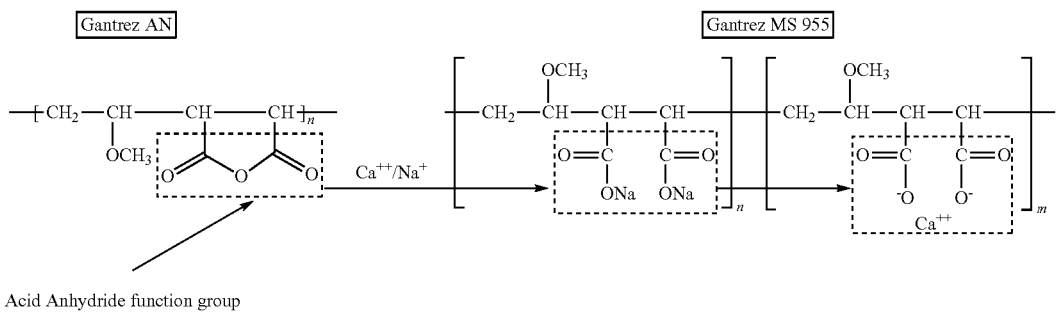

Acid Anhydride function group

Reaction Outlining the Formation of Gantrez MS 955

Alternative derivatives of this polymer can be manufactured by substituting various salt systems in the reaction as follows:

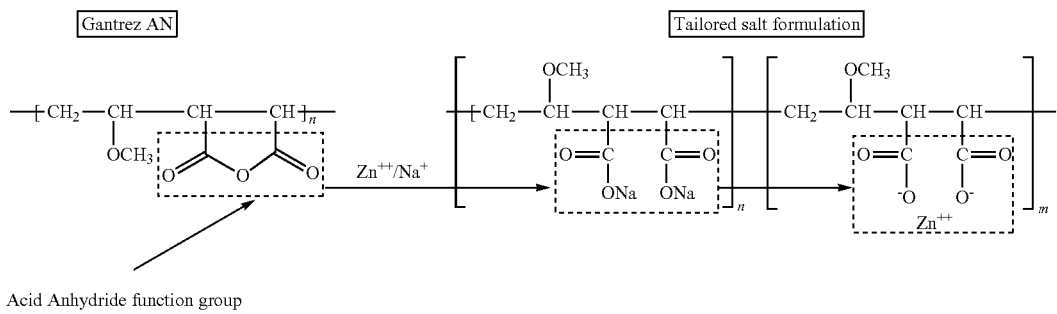

Acid Anhydride function group

Reaction Outlining the Formation of a Tailored Mixed Sodium/Zinc Salt Copolymer

Gantrez MS-955 polymer is slowly soluble in water. The divalent calcium ion lightly crosslinks the structure through ion bridges to reduce its solubility and increase its cohesive strength and viscoelasticity. The material has
- excellent wet adhesive strength;
- long-lasting hold; and
- mucoadhesive that enables delivery to mucous membranes This material has a molecular weight of 1,000,000 and the following chemical structure:

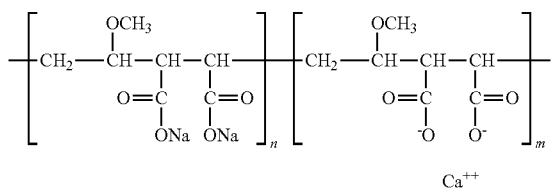

Chemical Structure of Gantrez MS-955

Experiment 3—Initial Solution Trials at Room Temperature 4 g of the polymer Gantrez MS-955 was added to 10 ml of deionised water and stirred.

Outcome: Dissolved and formed a paste (semi-solid).

4 g of the polymer was added to 10 ml of Milk and stirred.

Outcome: Dissolved and formed an adhesive paste.

Conclusion: The polymer reacted with the milk and an adhesive paste was produced.

Experiment 4—Distilled Water as a Delivery Mechanism 2 g of the polymer was added to 3 ml of water and stirred (600 rpm) at room temperature.

Outcome: Dissolved and formed a paste.

30 ml of distilled water was further added in stages to the solution and stirred.

Outcome: Thickened paste (increase in viscosity with addition of water).

Conclusion: Using distilled water as the delivery mechanism was not ideal as it made a very viscous paste, causing difficulty with injection.

Experiment 5—Liquid Paraffin as a Delivery Mechanism 2 g of the polymer was added to 3 ml of liquid paraffin and stirred (600 rpm) at room temperature.

Outcome: Encapsulated and formed a gel when injected, however it took a long time to do so.

Experiment 6—Ethanol as a Delivery Mechanism 3 g of the polymer was added to 2 ml of ethanol and stirred at 600 rpm at 37° C.

Outcome: viscous solution.

2 g of the polymer was further added to the solution and stirred.

Outcome: Thickened solution to form an injectable paste.

Conclusion: Initial trial with the syringe was a success relative to flowability.

Experiment 7—Optimise Ethanol Formulation

The following formulations were prepared.

Formulation Utilising Ethanol as a Delivery Vehicle

| 1 | 2 | 3 | 4 |
| --- | --- | --- | --- |
| Polymer/Ethanol | Polymer/Ethanol | Polymer/Ethanol | Polymer/Ethanol |
| 50/50 | 60/40 | 70/30 | 80/20 |
| 3 g/3 ml | 3.6 g/2.4 ml | 4.2 g/1.8 ml | 4.8 g/1.2 ml |

The samples were stirred at 600 rpm at a temperature of 37° C. for 10 minutes. The heat was then turned off, followed by another 20 minutes of stirring.

Outcome: Samples 1 and 2 were viscous. Sample 1 was chosen and injected into milk. This formed a paste and was placed in an oven at 40° C. After 3 days the sample still held after shaking, however, it has swollen. The sample was removed from the syringe and an adhesive paste remained.

Outcome: Sample 3 and 4 formed a dry paste. On addition of petroleum jelly (4 g), to sample four gave an injectable paste which was then injected into water and stored at 40° C. After 3 days the samples held after shaking.

Conclusion: Petroleum jelly has shown promise as a delivery mechanism.

Experiment 8—Investigate Petroleum Jelly as a Delivery Mechanism 5 g of petroleum jelly was heated to 60° C. (melt) and stirred at 600 rpm. 4 g of the polymer was gently added to the solution. The heat was turned off and the sample was allowed to stir for 30 minutes until cool.

Outcome: An injectable paste was formed and was subsequently injected into both water and milk. After 3 days (40° C.) the samples held after shaking. The sample was then removed after three days and a swollen adhesive paste remained.

Conclusion: Gantrez MS-955 reacted with the milk and an adhesive paste was produced.

Experiment 9—Stability Analysis Over a Temperature Range

A syringe was placed in a beaker at 37° C. and allowed to stabilise for ten minutes. The inside of the syringe was wetted and the formulation used in Experiment 6 was utilised. The syringe was submerged in the water and the seal held. Milk was then added and a magnetic flea was introduced at 100 rpm to agitate the syringe to represent teat movement. Over a period of 30 minutes the temperature was monitored.

TABLE 1

Temperature versus seal stability

| Temperature (° C.) | Seal Stability |
|---|---|
| 37 | Stable |
| 42 | Stable |
| 47 | Stable |
| 52 | Stable |
| 57 | Stable |
| 60 | Failure after 10 minutes |

Outcome: Stability was obtainable until the temperature reached 60° C.

Conclusion: This is a promising formulation and the failure at high temperature was probably due to melting of the petroleum jelly

Experiment 10—Stability Analysis at a Constant Temperature

A syringe was placed in a beaker at 37° C. and allowed to stabilise for ten minutes. The inside of the syringe was wetted and the formulation described in Experiment 6 was utilised. The syringe was submerged in the water and the seal held. Milk was then added and a magnetic flea was introduced at 50 rpm to agitate the syringe to represent teat movement. The results are as follows:

TABLE 2

Time versus seal stability

| | Time | Seal Stability |
|---|---|---|
| (27-28/5/2013) | 5:45-6:00 | Stable |
| | 6:00-6:15 | Stable |
| | 6:15-6:30 | Stable |
| | 6:30-6:45 | Stable |
| | 6:45-7:00 | Stable |
| | 7:00-7:15 | Stable |
| | 7:15-7:30 | Stable |
| | 7:30-7:45 | Stable |
| | 7:45-8:00 | Stable |
| | 8:00-8:00 | Stable |
| (28-29/5/2013) | 8:00-8:00 | Stable |
| (29-30/5/2013) | 8:00-8:00 | Stable |
| (30-31/5/2013) | 8:00-8:00 | Stable |
| (31/5/-4/6/2013) | 8:00-8:00 | Stable |
| (4-5/6/2013) | 8:00-8:00 | Stable |
| (5-6/6/2013) | 8:00-8:00 | Stable |
| (6-7/6/2013) | 8:00-8:00 | Stable |
| (7-10/6/2013) | 8:00-8:00 | Stable |
| (10-11/6/2013) | 8:00-8:00 | Stable |

Outcome: The seal was stable. To calculate the oscillation (which represents extreme teat movement) the magnet flea moved the syringe through a repeated cycle time. This was calculated based on the number of cycles completed per 10 seconds. The average results were calculated as shown below.

TABLE 3

Calculation of cycle time

| | Cycle Times | | | | | | | | | | |
|---|---|---|---|---|---|---|---|---|---|---|---|
| | 1 | 2 | 3 | 4 | 5 | 6 | 7 | 8 | 9 | 10 | |
| Time(Sec) | 10 | 10 | 10 | 10 | 10 | 10 | 10 | 10 | 10 | 10 | Average |
| Cycles | 17 | 18 | 18 | 17 | 16 | 17 | 17 | 16 | 17 | 17 | 17 |

Therefore,

Average 17 cycles per 10 Sec 102 cycles per 1 min 6,102 cycles per 1 hour

Thus, over a 14 hour period, there were 85,428 cycles (24 hours 146,880)

Conclusion: The formulation held under constant temperature and repeated oscillation. After 15 days the sample was removed and ejected. The compound contained the swollen matrix.

Objective: Stability test under a volume load.

Experiment 11—Stability Analysis at a Constant Temperature

The formulation from Experiment 6 was removed from the oven after 5 hours and placed under a volume of 3.5 litres of water.

TABLE 4

Stability analysis under load

| | Time | Seal Stability |
|---|---|---|
| (27-28/5/2013) | 5:00-8:00 | Stable |
| (28-29/5/2013) | 8:00-8:00 | Stable |
| (29-30/5/2013) | 8:00-8:00 | Stable |
| (30-31/5/2013) | 8:00-8:00 | Stable |
| (31/5/-4/6/2013) | 8:00-8:00 | Stable |
| (4-7/6/2013) | 8:00-8:00 | Stable |
| (7-10/6/2013) | 8:00-8:00 | Stable |

TABLE 4-continued

Stability analysis under load

| | Time | Seal Stability |
|---|---|---|
| (10-11/6/2013) | 8:00-8:00 | Stable |
| (11-12/6/2013) | 8:00-8:00 | Stable |
| (12-14/6/2013) | 8:00-8:00 | Stable |
| (14-17/6/2013) | 8:00-8:00 | Stable |
| (17-19/6/2013) | 8:00-8:00 | Stable |
| (19/6-04/7/2013) | 8:00-8:00 | Stable (46 days) |
| (4/7-12/7/2013) | 8:00-8:00 | Stable (54 days) |
| (12/7-15/7/2013) | 8:00-8:00 | Stable (57 days) Finish |

Outcome: The formulation has shown no signs of degrading. The seal held for 57 days.

TABLE 5

Percentage formulations used in vivo trials

| | Formulation | |
|---|---|---|
| | A | B |
| % W/W TS Base | 49.6 | 49.7 |
| % W/W Gantrez | 49.6 | 49.7 |
| % W/W Aerosil 200 | 0.8 | 0.6 |
| Ratio: Active:Base | 1:1 | 1:1 |

Two cows were infused, one containing the 0.6 Aerosil (coded 50:50(0.6)) and the other the 0.8 Aerosil (coded 50:50(0.8)). An antimicrobial was also infused with the formulations (Kefamast) and the findings are presented below:

TABLE 6

Results from the in vivo trials

| Day 1 | Day 6 |
|---|---|
| Infused Cow 1 after the last milking of her lactation as follows: | Cow 1-Formulation 50:50(0.8) |
| Front Right: Kefamast and Boviseal | Front Right: Boviseal stripped out completely |
| Front Left: Kefamast and formulation 50:50(0.8) | Front Left: formulation 50:50(0.8) seemed to strip out well |
| Rear Right: Kefamast and formulation 50:50(0.8) | Rear Right: No formulation 50:50(0.8) was visibly present |
| Rear Left: Kefamast and formulation 50:50(0.8) | Rear Left: Slight granules of formulation 50:50(0.8) could be felt lining the teat duct |
| Infused cow 2 after the last milking of her lactation as follows: | Cow 2 - Formulation 50:50(0.6) |
| Front Right: Kefamast and Boviseal | Front Right: Boviseal stripped out completely |
| Front Left: Kefamast and formulation 50:50(0.6) | Front Left: no formulation 50:50(0.6) was palpably left in the teat and milk was all that was seemingly stripped out |
| Rear Right: Kefamast and formulation 50:50(0.6) | Rear Right: Slight granules of formulation 50:50(0.6) could be felt lining the teat duct but not visible |
| Rear Left: Kefamast and formulation 50:50(0.6) | Rear Left: no formulation 50:50(0.6) was palpably left in the teat and milk was all that was obviously stripped out |

Conclusion: This formulation has shown promise both in milk at 37° C. and under volume.

In Vivo Trial 1

Formulations were then prepared and consisted of Gantrez MS955 in liquid paraffin/aluminium di-stearate (teat seal base) and Aerosil 200 as an emulsifier/thickening agent. This system formed reliable seals under in vitro conditions and showed no ingress of milk and demonstrated excellent bio-adhesive properties. These formulations were then prepared for gamma sterilisation at 25 kGy after which they were sent for in vivo trials.

The strength of the teat seal appeared to be dependent on Aerosil concentration with 0.8% Aerosil holding a seal in the front teat for 3 days during the in vivo trials. The 0.6% left a gelatinous residue once stripped from teat. In addition, studies undertaken displayed a relationship between Aerosil concentration and the viscosity measured. This relationship is temperature dependent with exponential behaviour visible at 20° C. while a linear relationship occurred at 37° C. The rheological data is presented in Table 7.

TABLE 7

Rheology of the 50-50 Gantrez: TS oil base

|  | Pre-Sterilisation Viscosity (Pas) at 20° C. | Post-Sterilisation Viscosity (Pas) at 20° C. | Pre-Sterilisation Viscosity (Pas) at 37° C. | Post-Sterilisation Viscosity (Pas) at 37° C. |
| --- | --- | --- | --- | --- |
| 0.8% Aerosil | 257.5 | 165.1 | 170.3 | 184.7 |
|  | 274.9 | 150.9 | 224.5 | 213 |
|  | 256.5 | 118.6 | 251 | 189.4 |
| Average | 262.96 | 144.86 | 215.26 | 195.7 |
| STV | 8.45 | 19.46 | 33.58 | 12.38 |
| 0.6% Aerosil | 211 | 147.3 | 178.2 | 190.1 |
|  | 230.6 | 154.1 | 209 | 218.2 |
|  | 221.4 | 137.2 | 187.7 | 171.6 |
| Average | 221 | 146.2 | 191.63 | 193.3 |
| STV | 8 | 6.94 | 12.87 | 19.15 |

|  | Pre 20° C. | Post 20° C. | % difference | Pre 37° C. | Post 37° C. | % difference |
| --- | --- | --- | --- | --- | --- | --- |
| 0.8 | 262.96 | 144.86 | −44.91 | 215.26 | 195.7 | −9.09 |
| 0.6 | 221 | 146.2 | −33.85 | 191.63 | 193.3 | 0.87 |

In Vivo Trial 2 The trial was repeated and the 50:50(0.8) sample was removed; however, there was no notable trace of the formulation present in the rear of the udder where 60% of the milk is carried. Neither cow showed any ill-effects during or in the few days after the study ended.

In Vivo Trial 3

The amount of Aerosil was increased to 1% and 1.5% respectively. Three formulations were prepared for in vivo trials as outlined. Formulation A and B had varying Aerosil concentrations while Formulation C incorporated Zinc oxide. Being hydrophobic in nature, Zinc oxide is a dense material (5.6 g/cm$^3$) and has multiple purposes including viscosity enhancer, antibacterial agent as well as radiopaque properties. For this trial, the samples were gamma sterilised at 7 kGy, as previous studies showed sterilisation had an effect on the rheological properties of the samples.

TABLE 8

Percentage formulations used in vivo trials

|  | Formulation | | |
| --- | --- | --- | --- |
|  | A | B | C |
| % W/W TS Base | 51.48 | 59.1 | 39.7 |
| % W/W Gantrez | 47.52 | 39.4 | 43 |
| % W/W Aerosil 200 | 1 | 1.5 | 0.8 |
| % W/W ZnO | N/A | N/A | 16.55 |
| Ratio: Active:Base | 0.92:1.08 | 1:1.5 | 1.5:1 |

TABLE 9

Rheology results pre-sterilisation
PRE-STERILISATION

| Formulation | Temperature | Viscosity | Formulation | Temperature | Viscosity | Formulation | Temperature | Viscosity |
| --- | --- | --- | --- | --- | --- | --- | --- | --- |
| A | 20° C. | 618.8 | B | 20° C. | 609.6 | C | 20° C. | 630.3 |
| A | 20° C. | 535.6 | B | 20° C. | 510 | C | 20° C. | 542.7 |
| A | 20° C. | 576.2 | B | 20° C. | 544.5 | C | 20° C. | 598.4 |
|  | Average | 576.8667 |  | Average | 554.7 |  | Average | 590.4667 |
|  | SDV | 33.96953 |  | SDV | 41.29625 |  | SDV | 36.19985 |
| A | 37° C. | 376.3 | B | 37° C. | 181.9 | C | 37° C. | 339.4 |
| A | 37° C. | 417.1 | B | 37° C. | 244.7 | C | 37° C. | 317.5 |
| A | 37° C. | 380.1 | B | 37° C. | 306.4 | C | 37° C. | 389.2 |
|  | Average | 391.1667 |  | Average | 244.3333 |  | Average | 348.7 |
|  | SDV | 18.40314 |  | SDV | 50.82757 |  | SDV | 30.001 |

TABLE 10

Rheology results post sterilisation
POST-STERILISATION

| Formulation | Temperature | Viscosity | Formulation | Temperature | Viscosity | Formulation | Temperature | Viscosity |
|---|---|---|---|---|---|---|---|---|
| A | 20° C. | 545.1 | B | 20° C. | 551.1 | C | 20° C. | 687.6 |
| A | 20° C. | 583 | B | 20° C. | 575.8 | C | 20° C. | 710.1 |
| A | 20° C. | 610.3 | B | 20° C. | 566.4 | C | 20° C. | 621.6 |
|  | Average | 579.4667 |  | Average | 564.4333 |  | Average | 673.1 |
|  | SDV | 26.73479 |  | SDV | 10.17917 |  | SDV | 37.55662 |
| A | 37° C. | 360.1 | B | 37° C. | 356.6 | C | 37° C. | 403.8 |
| A | 37° C. | 366.4 | B | 37° C. | 384.5 | C | 37° C. | 430.2 |
| A | 37° C. | 372.6 | B | 37° C. | 369.2 | C | 37° C. | 441.1 |
|  | Average | 366.3667 |  | Average | 370.1 |  | Average | 425.0333 |
|  | SDV | 5.103158 |  | SDV | 11.40789 |  | SDV | 15.65979 |

All three formulations were infused into cows. After a 5 day period, each formulation was stripped out from the back teat, where milk production is more significant. A small amount of Formulation A was retrieved. Formulation B was not present and Formulation C was successfully removed.

Increasing concentration of Aerosil failed to produce a good seal. This could be attributed the "hydrophilic" nature of Aerosil or/and that fact that a good seal is concentration dependent. [Aerosil concentrations above 0.8% previously displayed a significant change in viscosity].

The ratio of active (Gantrez/Zinc Oxide) to the TS Base appears to be very important in achieving a good seal. Lowering the Gantrez concentration may lead to loss in the bio-adhesive nature of the formulation. In addition the use of TS base works well at low concentrations when used as emollient, however, increasing the amount beyond 50% leads to a greasy or oilier paste. This in turn will have a negative effect on bio-adhesive nature of the seal.

The introduction of ZnO led to a successful teat seal. ZnO appears to react with Gantrez giving a swollen structure on removal. The degree of swelling itself may be cause for excellent teat seal.

Following irradiation at 7 kGy the viscosity of Formulation C with Zinc Oxide increased at both 20 and 37 degrees Celsius. This is indicative of chemical binding/crosslinking of the Zinc Oxide and Gantrez and potentially is the foundation of a superior teat seal.

Gantrez/Metallic Oxide Formulation Development

From the trial described above, the synergistic mixture of the Gantrez based polymer with the Zinc Oxide shows promise. To achieve a better understanding of the interactions between the Gantrez and the metallic viscosity/rheometry studies as well as compression testing were employed to characterise the formulations. This was completed in conjunction with previous work by taking metallic oxides of similar densities and integrating them into predetermined formulations. A range of formulations were then prepared by varying both the composition and concentrations of the various constituents in order to determine their effect on both viscosity and ease of administration (compression testing). The base was also changed to test its effect on the ease of administration, with the emphasis being on the structural effects of composition dependency. Typical bases included liquid paraffin oil and 1-Oleoyl-rac-glycerol, while three metal oxides were examined namely Zirconium Oxide, Titanium Dioxide and Zinc Oxide. Variations of the Gantrez, Metal Oxides and base were formulated and evaluated.

TABLE 11

Viscosity and Injection Force results

| | Composition | | | | Results | |
|---|---|---|---|---|---|---|
| Testing Sample | Gantrez MS955 (%) | Metal oxide (%) | Base (%) | Additive (%) | Viscosity (Pa · S) @ 20° C. | Max Load/Force (Newton)* |
| SEAL Formulation | N/A | N/A | N/A | Aerosil | 70.00 | 32.908 |
| A | 25 | Zinc Oxide 25 | liquid Paraffin 49.5 | Aerosil 0.5 | 399.36 | 35.38 |
| B | 25 | Zirconium Oxide 25 | liquid Paraffin 49.5 | Aerosil 0.5 | 37.04 | 27.03 |
| C | 25 | Titanium Dioxide 25 | liquid Paraffin 49.5 | Aerosil 0.5 | 130.43 | 89.792 |
| D | 20 | Zinc Oxide 30 | liquid Paraffin 49.5 | Aerosil 0.5 | 464.76 | 41.35 |
| E | 30 | Zinc Oxide 20 | liquid Paraffin 49.5 | Aerosil 0.5 | 241.37 | 41.33 |
| F | 25 | Zinc Oxide 25 | 1-Oleoyl-rac-glycerol 49.5 | Aerosil 0.5 | 23.03 | 38.86 |

TABLE 11-continued

Viscosity and Injection Force results

| Testing Sample | Composition | | | | Results | |
|---|---|---|---|---|---|---|
| | Gantrez MS955 (%) | Metal oxide (%) | Base (%) | Additive (%) | Viscosity (Pa · S) @ 20° C. | Max Load/Force (Newton)* |
| G | 34.4 | Zinc Oxide 34.4 | 1-Oleoyl-rac-glycerol 30.8 | Aerosil 0.4 | 92.68 | 113.01 |
| H | 29.75 | Zinc Oxide 29.75 | liquid Paraffin 40.0 | Aerosil 0.5 | 1450 | 64.22 |

From the above results it appears that viscosity and ease of administration are not related and is solely composition dependant. For example, Formulation A, B and C are all similar in composition and concentration except each formulation contains a different metal oxide (each metal oxide had similar densities). Zirconium Dioxide yields the lowest viscosity and the max force load needed to express sample was 27 Newton. However, in spite of Titanium Dioxide and Zinc Oxide yielding a viscosity of 140 and 413 Pa·s respectively, the Zinc Oxide formulation was substantially easier to express. These results indicate composition is a primary factor to characterise the ease of administration. The use of 1-Oleoyl-rac-glycerol in place of liquid paraffin resulted in change in viscosity from 413 to 23 Pa·s. However, the formulation was substantially harder to express. The higher the Zinc Oxide concentration in the 1-Oleoyl-rac-glycerol based systems the harder the formulations were to express.

Large differences in the viscosity and the force required to express the various formulations indicated that the viscosity is not a measure or related indirectly to the difficulty of expressing a sample from a syringe (unless all formulations utilise the same constituents). In addition all of the metal oxides have similar densities of around 5 g/cm$^3$; however, Zirconium Dioxide is known for been chemically un-reactive and this is further substantiated by Formulation B which provided a viscosity of 37 Pa·s. In contrast, Zinc Oxide yielded a viscosity of 413 Pa·s and this is a result of chemical interactions with the Gantrez, which subsequently progressed to crosslinking within the formulation; thus increasing the viscosity. A viscosity of 130 Pa·s was found for Titanium Dioxide which is indicative of physical interactions, mainly due to the polarity of the molecule. Based on the formulations, four samples were selected. It was decided to further investigate two particular formulations, namely (A) and (E).

A trial was devised to examine Formulations (A) and (E) exposed to two sterilisation cycles (7 and 25 kGy).

Rheological Analysis of Formulations (A) and (E)

A large reduction in the viscosity post sterilisation was evident in all samples.

On analysing the rheological results, a 54% reduction in viscosity for Formulation (A) occurred at 20° C. when the samples were sterilised at 7 KGy. By increasing the temperature to 37° C., the viscosity decreased from 219.53 to 66.07 Pa·s (69.9% reduction). When Formulation (A) was sterilised at 25 KGy, once again, the viscosities decreased at both test temperatures (see Table 30). Overall, there was a reduction of 81% in the viscosity from the pre-sterilised sample at 20° C. to the post sterilised 7 KGy sample tested at 37° C. When the 25 KGy samples were evaluated, a 75% reduction in the viscosity was noted.

This reduction in the viscosity is perceived to be a result of the chemical scission of the crosslinks via gamma exposure. Similar findings were found in Formulation (E). However, a 68% reduction was noted in the viscosity for the pre-sterilised samples tested at 20° C. to the post sterilised samples at 37° C. Considering Formulation (E) had a 5% lower concentration of ZnO compared to (A), it would suggest that reducing the concentration of ZnO would be beneficial. The concentration of ZnO used in the in vivo trial is believed to be a contributing factor in the breakdown of the formulation.

TABLE 12

Viscosity evaluation of Formulation (A) and (E)

| | Pre 20° C. | Post (7KGy) 20° C. | % difference |
|---|---|---|---|
| A | 351.25 | 160.32 | −54.36 |
| E | 266.62 | 110.46 | −58.57 |

| | Pre 37° C. | Post (7KGy) 37° C. | % difference |
|---|---|---|---|
| A | 219.53 | 66.07 | −69.90 |
| E | 174.08 | 85.31 | −50.99 |

| | Pre 20° C. | Post (25 KGy) 20° C. | % difference |
|---|---|---|---|
| A | 351.25 | 122.1 | −65.24 |
| E | 266.62 | 89.12 | −66.57 |

| | Pre 37° C. | Post (25 KGy) 37° C. | % difference |
|---|---|---|---|
| A | 219.53 | 86.07 | −60.79 |
| E | 174.08 | 85.13 | −51.10 |

| | Pre 20° C. | Post (7KGy) 37° C. | % difference |
|---|---|---|---|
| A | 351.25 | 66.07 | −81.19 |
| E | 266.62 | 85.31 | −68.00 |

| | Pre 20° C. | Post (25KGy) 37° C. | % difference |
|---|---|---|---|
| A | 351.25 | 86.07 | −75.50 |
| E | 266.62 | 85.13 | −68.07 |

Evaluation of the Administration of Formulation (A) and (E) from a Syringe

Based on the test, comparative analysis on the compression/injection force from the syringes was evaluated. A Lloyd LRX tensile tester was employed in compression mode with a load cell of 2500N to measure the force required to express a formulation from the syringe, the samples were tested at room temperature. Initially tests were carried out on empty syringes to measure the distance travelled by the plunger within the. A distance of 60 mm was obtained from measuring samples from the top of the barrel to the top of the plunger. The distance travelled by the plunger within the barrel of the syringe was found to be 47.5 mm. A test was designed to accommodate the syringe and machine set. Eight formulations in total were prepared each with varying concentration and components. The force required to express each paste was measured a minimum of 5 times.

The time taken as well as the formulation content has an overall effect on the administration force. This was more evident in the Bimeda Boviseal formulation, where an injection time of 5.7 seconds had a max force of 61N compared to a 34N force when administered at 9.5 seconds. The difference is explained by the higher density of the Bismuth present in the Bimeda formulation which upon the application of a high shear (faster injection time), packs the material at the front of the nozzle. Thus, more force is required to push the formulation through the channel of the nozzle. A slower time allows the material to flow much easier and as a result this reduces the max force of insertion. Formulations (A) and (E) were more consistent during the time trials but did exhibit varying injection profiles.

Taking a standard injection speed of 300 mm/min (9.5 sec), the max load (force) between the samples was investigated. There were no significant differences between the samples. However, sterilisation has altered the flow properties of the formulation. In relation to the work at the max load, the Bimeda Boviseal sample is significantly larger when compared to the other formulations and this is due to the higher density of the Bismuth which requires more energy upon formula delivery.

In relation to the sterilised samples, the ratio of Gantrez to ZnO appears to be very important as this can alter both the viscosity and injection force requirements. In the case of Formulation (A) which has a 25%/25% Gantrez/ZnO component, dose rates of both 7 and 25 KGy reduced the viscosity of the samples. However, a 7 KGy dose rate decreased the injection force in contrast to the 25 KGy which increased the injection force. The inverse is true for Formulation (E), which has a 30%/20% Gantrez/ZnO component. Although there are two flow properties being evaluated (viscosity and injection force), the thixotropic nature of the formulations behaves differently under shear conditions. FIG. 1 illustrates the effects of viscosity is noticeable compared to the Max Injection forces.

Bio-Adhesion Analysis

Figure 2:
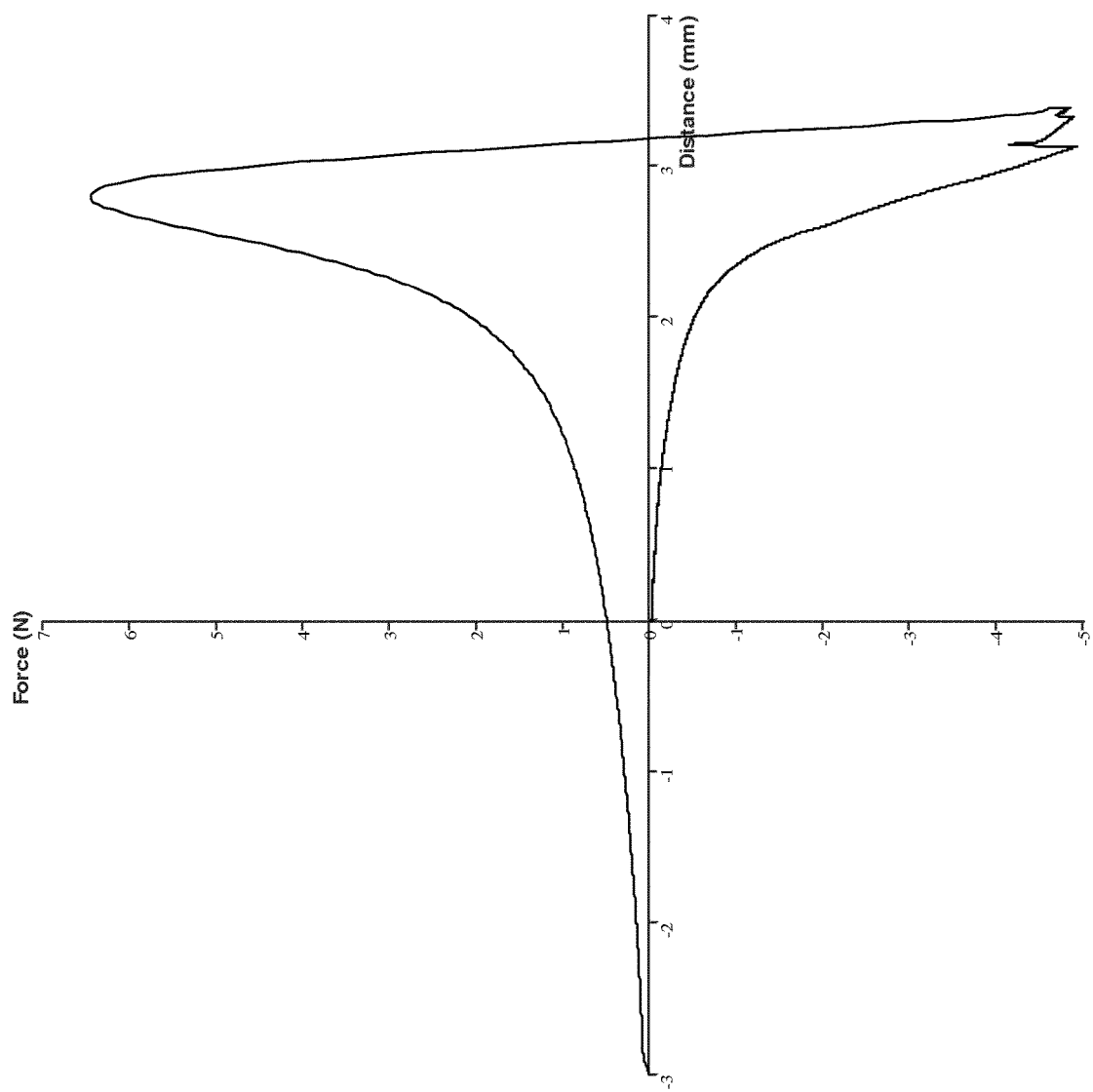
FIG. 2 shows typical adhesive graphs obtained from the bio-adhesion study. The sample is Formulation A (pre-sterilised).

Bio-adhesion studies were carried out to evaluate the adhesive nature of the formulations. The Instrument was a Texture Analyser from Stable Micro Systems and a predetermined program was selected which was based on the measurement of an adhesive gum. The instrument was calibrated with a 1000 g weight and a 92% confidence interval was obtained using a P/36R-aluminium Probe. A typical graph obtained from the work is presented in FIG. 2. The main findings are as follows:

Mixing formulations with milk displayed bio-adhesive properties. However, this was not visible in formulations which did not have the milk present as well as the particular grade of Gantrez used.

All formulations increased in bio-adhesiveness with Gantrez concentration.

Greater adhesive properties seen after sterilisation.

Form X had good adhesive properties

TABLE 13

Formulations used in the Bio-adhesion study (1)

| Sample | Gantrez (%) | Zinc oxide (%) | Base (%) | Aerosil (%) | Additive |
|---|---|---|---|---|---|
| Original | 59.5 | N/A | 39.7 | 0.8 | N/A |
| Form C | 43 | 16.5 | 39.7 | 0.8 | N/A |
| Form X | 25 | 25 | 32.8 | 0.5 | 16.7% of 1-Oleoyl-rac-glycerol |
| Form A | 25 | 25 | 49.5 | 0.5 | N/A |
| Form E | 30 | 20 | 49.5 | 0.5 | N/A |

A second Bio-adhesion Study was carried out to evaluate alternative to the Gantrez MS955.

TABLE 14

Formulations used in the Bio-adhesion study (2)

| Formulation | Gantrez | Zinc oxide (%) | liquid paraffin oil (%) | Aerosil (%) | Additive (%) |
|---|---|---|---|---|---|
| F | MS955 40% | 10 | 49.5 | 0.5 | N/A |
| G | AN169 20.5% | 14 | 62 | 0.5 | N/A |
| H | Gantrez S97-P 30% | 20 | 49.5 | 0.5 | N/A |

The main findings are as follows;

Formulation F: Paste like with no noticeable adhesive properties.

Formulation G: Very adhesive on appearance also due to its high molecular weight, as less polymer was needed.

Formulation H: Non-adhesive in appearance. However, there was an apparent increase in viscosity when left overnight.

Each of the above formulations were then mixed with 2 ml of milk to mimic in vivo conditions and then bio-adhesion was retested.

Formulation F: Increase in elasticity following mixing with milk. The formulation had good adhesion and cohesiveness and did not break up.

Formulation G: An increase in time and shear was required to form a paste. This was less viscous and it was apparent that no crosslinking occurred.

Formulation H: Extremely adhesive (most adhesive formulation to date), did not break up. However, it was difficult to express the formulation from syringes.

Each of pure Gantrez polymers were also tested with milk and the findings are;

MS955 with 4 ml milk . . . v adhesive

AN169 with 4 ml milk . . . not miscible with milk insoluble no reaction

MS97-P with 4 ml milk . . . adhesive properties visible

Radiopacity Testing

The aim of this study was to determine the radiopaque quality or limit of detection of formulations at various concentrations of active (Zinc Oxide). X-Ray images were taken of each sample. A metal circular coin was placed in the images as a marker.

TABLE 15

Formulations used in the Radiopacity study

| | Formulation (%) | | |
|---|---|---|---|
| | 1 | 2 | 3 |
| Gantrez MS955 | 30 | 40 | 45 |
| Zinc Oxide | 20 | 10 | 5 |
| Aerosil | 0.5 | 0.5 | 0.5 |
| Liquid Paraffin | 49.5 | 49.5 | 49.5 |

An X-ray image of a pure sample of Gantrez MS955 was taken for comparative purposes. Due to low density of the polymer, poor radiopaque visibility was witnessed. The three formulations made by varying the concentration of Zinc Oxide which has a density of 5.61 g/cm$^3$ were tested. From the images, a clear pattern emerged whereby the higher the concentration of Zinc Oxide, the darker or easier the image is detected by X-ray. However, at concentrations as low as 5%, Zinc Oxide is still apparent in the images, which could be beneficial in formulation design.

Other Metal Oxides

To test the hypothesis that Zinc Oxide (ZnO) was reacting with the Gantrez, a number of similar Metal Oxides with comparable densities was chosen for analysis. Keeping with the same concentration, each Metal Oxide was substituted into the same base formula. Zirconium Dioxide is known to be chemically unreactive and this is further substantiated by Formulation B (refer to table 11) which yielded a viscosity of 37 Pa·s compared to Zinc Oxide which yielded a viscosity of 413 Pa·s. This shows that the ZnO reacted with the Gantrez which subsequently progressed to crosslinking within the formulation; thus increasing the viscosity. Titanium Dioxide yielded a viscosity of 130 Pa·s which is indicative of the physical interactions, mainly due to the polarity of the molecule.

The reduction in the viscosity is postulated to be a result of the chemical scission of the crosslinked structure via gamma exposure. Similar findings were found in Formulation (E), however, a 68% reduction was noted. Considering Formulation (E) had a 5% lower concentration of ZnO compared to (A), it would suggest that reducing the concentration of ZnO would be beneficial. Only one formulation (E7) was deemed recoverable from the animals, but this was not consistent. The concentration of ZnO used in vivo trial 5 is considered to be a contributing factor in the breakdown of the formulation.

In relation to sterilisation, the ratio of Gantrez to ZnO is very important. Looking at Formulation (A) which has a 25%/25% Gantrez/ZnO component, dose rates of both 7 and 25 KGy reduced the viscosity of the samples. With regard to the injection administration study, a 7 KGy dose rate decreased the injection force. In contrast, the 25 KGy exposure to Formulation (A) increased the injection force. The inverse is true for Formulation (E), which has a 30%/20% Gantrez/ZnO composition. Thus, it's worth noting that the thixotropic nature of the formulations behaves differently under shear conditions. It is for this reason such variability exists and further optimisation will be required in working out the optimal Gantrez/ZnO ratios in a desired base under set gamma dose rates.

Mixing formulations which contained the MS955 grade of Gantrez with milk displayed bio-adhesive properties.

All formulations increased in bio-adhesiveness with Gantrez concentration.

Greater adhesive properties seen after sterilisation.

At concentrations as low as 5%, Zinc Oxide is still apparent in the radiopaque images, which could be beneficial in formulation design.

Chemical Reactions

Gantrez MS955

Gantrez MS-955 polymer is a mixed sodium and calcium salt of methyl vinyl ether and maleic anhydride copolymer supplied as a powder. The polymer is slowly soluble in water resulting in amber-coloured solutions with high viscosity and adhesion. The divalent calcium ion lightly crosslinks the material through ion bridges to reduce its solubility and increase its cohesive strength and viscoelasticity. It is believed that the repeating units may be represented as:

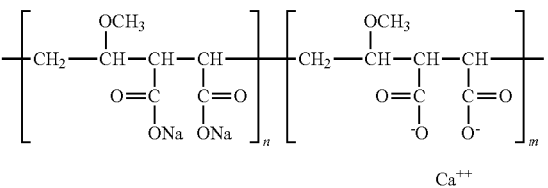

Chemical Repeat Unit of Gantrez MS955 outlining the Calcium Ions

Therefore, in the presence of Milk, in vivo or an aqueous environment two reactions will occur:

a) Calcium bridging will lightly crosslink the structure, thus increasing elasticity, adhesiveness and viscosity.

b) Bronsted lowry acid base theory; Gantrez MS-955 is not readily biodegradable but will slowly degrade to simple carbon compounds through biological and abiotic processes.

One such abiotic process is hydrolysis. A common kind of hydrolysis is that of a salt of a weak acid or base. Water spontaneously ionizes into hydroxide anions and hydrogen cations. The salt too dissociates into its constituent anions and cations. In this particular case Na+ and an ester. An Hydrogen ion reacts with ester to produce an acid product while cations react slowly but very little with hydroxide

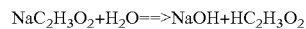

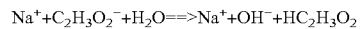

Since NaOH is a strong base it breaks up and yields OH$^-$, the salt is basic.

HC$_2$H$_3$O$_2$ is a weak acid and will form (does not break up in water).

Reactions Among Excipients and Gantrez within the Formulations

1) Bronsted Lowry Acid Base Theory

Zinc Oxide is an amphoteric oxide and therefore can act as both an acid and base. Once Gantrez has reverted to carboxylic acid, Zinc Oxide will react to form a salt and water. (ZNO is degraded by most acids).

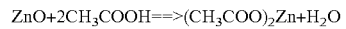

Note ZnO will also react slowly with fatty acids in oils (1-Oleoyl-rac-glycerol) to produce the corresponding carboxylates, such as oleate or stearate.

2) Esterification

Esters are chemical compounds consisting of a carbonyl adjacent to an ether linkage. They are derived by reacting an oxoacid with a hydroxyl compound such as an alcohol or phenol. Therefore, any such polyols for example glycerol will react with acid groups in Gantrez post hydrolysis thereby producing an ester with increased viscosity. The esterification reaction is both slow and reversible. The equation for the reaction between an acid RCOOH and an alcohol R'OH (where R and R' can be the same or different) is:

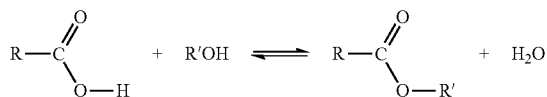

Equation for the Reaction Between an Acid RCOOH and an Alcohol R'OH

Manufacturing Process 1

The process for preparation of an adhesive teat seal firstly involved mixing the specified amount of mixed salt of PVA/MA (Gantrez) (bio-adhesive polymer) co-polymer with an emulsifier namely Aerosil 200 and Zinc Oxide. All additives are slowly agitated until uniformly dispersed. The final stage involved adding a wetting agent or emollient either liquid paraffin or TS base (alugel based liquid paraffin while continuously agitating the mixture). Whilst manufacturing procedure is carried out in that order, it is not limited to that order. In fact on scaling up it may be of benefit to slowly add the Gantrez last into an oil based dispersion in order to control the rate of reaction. This step is of particular importance if using Gantrez S97 powder.

Note: Continuous stirring should be used once liquid paraffin added.

Mixing Equipment used: Heildolph Mixer at 200 rpm

Hotplate with magnetic stirrer or manually stirred on small scale

Manufacturing Process 2

The objective of this process is to induce a heating reaction to catalyse chemical crosslinking. Formulation was made by first placing polyol (glycerol) in a main vessel. Gantrez MS 955 is added to the polyol, while heating to 75° C.; and is mixed until uniform. At 70-75° C., Aerosil is added and the composition and mixed until uniform, adjusting agitation to facilitate good turnover. The vessel is removed from heat and with moderate agitation; the Zinc Oxide followed immediately by liquid paraffin oil is added with continuous stirring throughout addition of reactants. Mixing is continued at a lower level of agitation until uniform. The resulting product is a paste-like with excellent spreadable and bio-adhesives properties.

TABLE 16

Percentage formulations used to prepare Formulation C

|  | Formulation C |
| --- | --- |
| % W/W TS Base | 39.7 |
| % W/W Gantrez | 43 |
| % W/W Aerosil 200 | 0.8 |
| % W/W ZNO | 16.55 |
| Ratio: Active:Base | 1.5:1 |

The ratio of active (Gantrez/Zinc Oxide) to the TS Base appears to be important in achieving a good seal. Lowering the Gantrez concentration may lead to loss in the bio-adhesive nature of formulation. The use of teat seal base works well at low concentrations when used as emollient, however, increasing the amount beyond 50% leads to greasy or oilier paste. This in turn will have a negative effect on bio-adhesive nature of the seal.

A formulation having high density/viscosity is required. However, if the viscosity is too high there is decreased compliance or easy application of teat seal. There are 4 additives which appear to have an influence on the viscosity of formulations;

Zinc oxide

Aerosil

Gantrez

Alugel in Base

By varying these concentrations in the formulation as shown in Table 17, it is expected that a seal with all of the desired characteristics can be achieved. Gamma sterilisation chemically and physically alters the structure of the formulation. Chain scission may occur as a result of irradiation which is reflected by the reduction in viscosity of the materials. Gamma sterilisation may also induce crosslinking and this may be used to manipulate the formulation.

TABLE 17

Proposed range of additives

| Material | Proposed range (%) |
| --- | --- |
| Gantrez MS955 | 30-55 |
| Zinc Oxide | 5-20 |
| Aerosil | 0.4-0.8 |
| Base | 30-50 |

The invention is not limited to the embodiments hereinbefore described, which may be varied in detail.

The invention claimed is:

1. A seal formulation for forming a physical barrier in the teat canal of a non-human animal comprising a polymer in a gel base
    wherein the polymer is mixed calcium and sodium salt derivative of a methyl vinyl ether-maleic anhydride copolymer, and
    wherein the seal formulation further comprises a viscosity enhancing agent that comprises zinc oxide, and
    wherein the ratio of the sum of the weight percent of polymer and the weight percent of the zinc oxide to the weight percent of the gel base is from 1.5:1 to 1:1.5.

2. The seal formulation as claimed in claim 1, wherein the seal formulation contains from 10% to 60% by weight of the polymer.

3. The seal formulation as claimed in claim 1, wherein the seal formulation contains from 20% to 60% by weight of the polymer.

4. The seal formulation as claimed in claim 1, wherein the seal formulation contains from 30% to 55% by weight of the polymer.

5. The seal formulation as claimed in claim 1, wherein the seal formulation contains from 1% to 35% of the viscosity enhancing agent.

6. The seal formulation as claimed in claim 1, wherein the seal formulation contains from 5% to 25% of the viscosity enhancing agent.

7. The seal formulation as claimed in claim 1, wherein the seal formulation contains from 5% to 20% of the viscosity enhancing agent.

8. The seal formulation as claimed in claim 1, which further comprises a thixotrophic agent.

9. The seal formulation as claimed in claim 8, wherein the seal formulation contains from 0.1% to 1% of the thixotrophic agent.

10. The seal formulation as claimed in claim 8, wherein the seal formulation contains from 0.4 to 0.8% of the thixotrophic agent.

11. The seal formulation as claimed in claim 8, wherein the thixotrophic agent comprises fumed silica.

12. The seal formulation as claimed in claim 1, wherein the base is a gel based on aluminium stearate.

13. The seal formulation as claimed in claim 1, wherein the base includes liquid paraffin as a vehicle.

14. The seal formulation as claimed in claim 1, wherein the seal formulation contains from 30% to 50% of the base.

15. The seal formulation as claimed in claim 1, wherein the ratio of the sum of the weight percent of polymer and the weight percent of the zinc oxide to the weight percent of the gel base is 1.5:1.

16. The seal formulation as claimed in claim 1, wherein the seal formulation has been irradiated.

17. The seal formulation as claimed in claim 16, wherein the seal formulation has been irradiated at 7 kGy.

18. The seal formulation as claimed in claim 16, wherein the seal formulation has been irradiated at 25 kGy.

* * * * *

UNITED STATES PATENT AND TRADEMARK OFFICE
CERTIFICATE OF CORRECTION

| | |
|---|---|
| PATENT NO. | : 11,571,442 B2 |
| APPLICATION NO. | : 15/771884 |
| DATED | : February 7, 2023 |
| INVENTOR(S) | : Francisco Javier Molins Albanell et al. |

It is certified that error appears in the above-identified patent and that said Letters Patent is hereby corrected as shown below:

On the Title Page

Item (71), in the Applicant, Lines 1-2, "Zoetis Broomhill IP Limited, County Dublin (IE)" should read --Zoetis Broomhill IP Limited, Loughlinstown (IE)--.

Signed and Sealed this
Twenty-first Day of March, 2023

Katherine Kelly Vidal
Director of the United States Patent and Trademark Office